US012657704B2

(12) United States Patent
Wang et al.

(10) Patent No.: US 12,657,704 B2
(45) Date of Patent: Jun. 16, 2026

(54) TIME PHASE DETERMINATION APPARATUS AND TIME PHASE DETERMINATION METHOD

(71) Applicant: CANON MEDICAL SYSTEMS CORPORATION, Tochigi (JP)

(72) Inventors: Chunqi Wang, Beijing (CN); Hong Yang, Beijing (CN); Yutaka Hoshiyama, Nasushiobara (JP)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 487 days.

(21) Appl. No.: 18/300,460

(22) Filed: Apr. 14, 2023

(65) Prior Publication Data

US 2023/0342926 A1    Oct. 26, 2023

(30) Foreign Application Priority Data

Apr. 26, 2022    (CN) .......................... 202210446901.8
Mar. 8, 2023    (JP) ................................. 2023-035605

(51) Int. Cl.
*G06T 7/00*        (2017.01)
*A61B 5/00*        (2006.01)
*A61B 6/00*        (2006.01)

(52) U.S. Cl.
CPC .......... *G06T 7/0012* (2013.01); *A61B 5/0037* (2013.01); *A61B 6/481* (2013.01);
(Continued)

(58) Field of Classification Search
None
See application file for complete search history.

(56) References Cited

U.S. PATENT DOCUMENTS 8,872,822 B2 * 10/2014 Ekin ......................... G06T 7/11
345/424
9,280,817 B2    3/2016 Yoshikawa
(Continued)

FOREIGN PATENT DOCUMENTS

CN        109952063 A    6/2019

OTHER PUBLICATIONS

Spincemaille et al., "Automated Detection of the Optimal Arterial Phase in Dynamic 3D Contrast Enhanced Imaging of the Liver", ISMRM 21, 1536, 2013, 1 page.

(Continued)

*Primary Examiner* — Anand P Bhatnagar
(74) *Attorney, Agent, or Firm* — Oblon, McClelland, Maier & Neustadt, L.L.P.

(57)        ABSTRACT

A time phase determination apparatus according to an embodiment is a time phase determination apparatus for determining the range of a particular time phase in a contrast-enhanced image, and includes processing circuitry. The processing circuitry acquires medical images at a plurality of different timings. The processing circuitry extracts a plurality of regions of interest on the basis of the medical images at the different timings. The processing circuitry generates a plurality of time intensity curves that are time intensity curves corresponding to the respective regions of interest. The processing circuitry determines the range of the particular time phase on the basis of the time intensity curves.

15 Claims, 7 Drawing Sheets

(52) U.S. Cl.
CPC .............. *G06T 2207/30056* (2013.01); *G06T 2207/30084* (2013.01)

(56) References Cited

U.S. PATENT DOCUMENTS

| | | | |
|---|---|---|---|
| 10,736,593 B2 * | 8/2020 | Yao ........................ | A61B 6/022 |
| 11,823,387 B2 * | 11/2023 | Kaethner .............. | A61B 6/504 |
| 12,112,481 B2 * | 10/2024 | Kim ...................... | G06T 7/0012 |
| 12,376,750 B2 * | 8/2025 | Madabhushi ...... | A61B 5/02007 |
| 12,376,783 B2 * | 8/2025 | Riley .................. | A61B 5/4064 |
| 12,376,789 B2 * | 8/2025 | Kwon .................. | A61B 5/4088 |
| 12,376,813 B2 * | 8/2025 | Tobón Gómez ....... | A61B 6/504 |
| 12,380,314 B2 * | 8/2025 | Dube ...................... | G06T 7/149 |
| 12,380,555 B2 * | 8/2025 | Chuang .................... | G06N 3/08 |
| 12,380,556 B2 * | 8/2025 | Xin ...................... | G06T 7/0012 |
| 12,380,584 B2 * | 8/2025 | Hendriks ............. | G06T 7/0012 |
| 2022/0005240 A1 * | 1/2022 | Shinoda ................ | A61B 5/004 |
| 2023/0186474 A1 * | 6/2023 | Kim .................... | A61B 5/0033 |
| | | | 382/130 |

OTHER PUBLICATIONS

Ma et al., "Automated Identification of Optimal Portal Venous Phase Timing with Convolutional Neural Networks" Academic Radiology, 27(2), 2020, 9 pages.
Office Action issued Mar. 10, 2026, in corresponding Chinese Patent Application No. 202201446901.8, 9 pages.

* cited by examiner

TIME PHASE DETERMINATION APPARATUS 100

| ACQUISITION UNIT 101 | TARGET EXTRACTION UNIT 102 |
|---|---|
| GENERATION UNIT 103 | TIME PHASE DETERMINATION UNIT 104 |

START

ACQUIRE MEDICAL IMAGES — S101

EXTRACT REGIONS OF INTEREST — S102

GENERATE TIC — S103

DETERMINE RANGE OF PARTICULAR TIME PHASE — S104

END

TIME PHASE DETERMINATION APPARATUS 100

ACQUISITION UNIT 101

TARGET EXTRACTION UNIT 102

GENERATION UNIT 103

TIME PHASE DETER-MINATION UNIT 104

IMAGE RECONSTRUC-TION UNIT 105

START

TRACK RIGID BODY MOTION OF ENTIRE AREA OF LIVER AREA — S210

CALCULATE DISPLACEMENT OF LIVER AREA RELATIVE TO ENTIRE AREA OF LIVER AREA FOR EACH MEDICAL IMAGE — S220

END

S210

EXTRACT LOCAL TARGETS AT EXTREME POINTS    S221

EXTRACT LOCAL TARGETS AT OTHER POSITIONS    S222

PREDICT DISPLACEMENT OF EACH LOCAL TARGET    S223

CALCULATE LIVER AREA AFTER DEFORMATION    S224

END

TIC OF ABDOMINAL AORTA

FIG.10
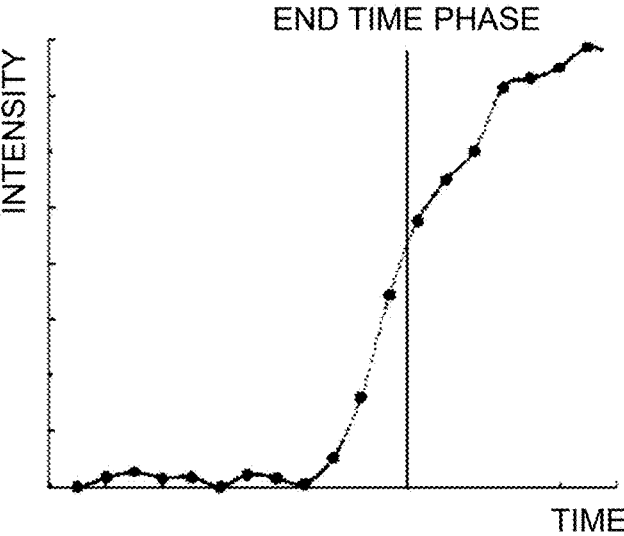
TIC OF LIVER
FIG.11A
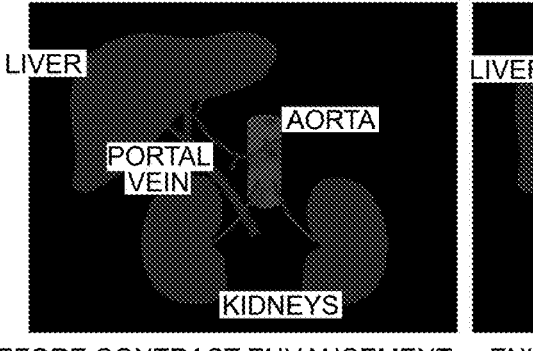
BEFORE CONTRAST ENHANCEMENT
FIG.11B
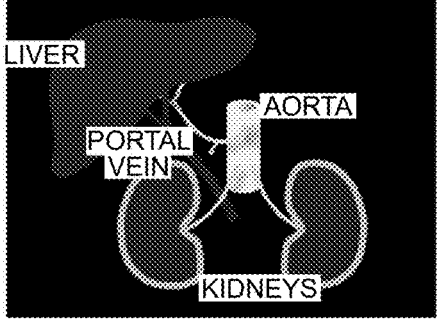
ENHANCED ABDOMINAL AORTA
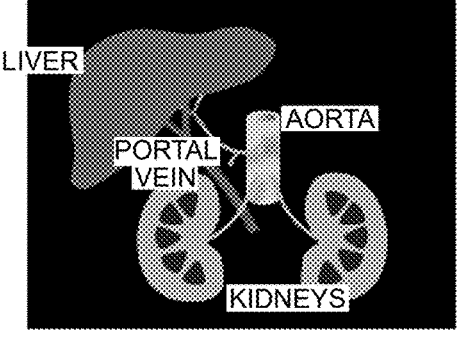
ENHANCED KIDNEYS
FIG.11C
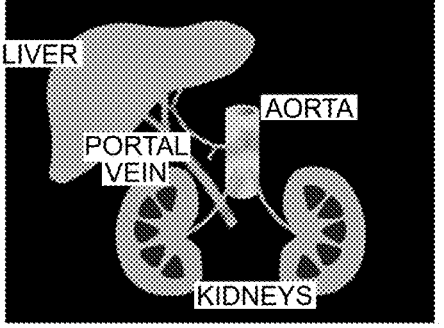
ENHANCED LIVER
FIG.11D
EXAMPLE OF ORDER OF ENHANCING REGIONS OF INTEREST

TIC FOR KIDNEY-LIVER INTENSITY DIFFERENCE

TIME PHASE DETERMINATION APPARATUS AND TIME PHASE DETERMINATION METHOD

CROSS-REFERENCE TO RELATED APPLICATIONS

This application is based upon and claims the benefit of priorities from Chinese Patent Application No. 202210446901.8, filed on Apr. 26, 2022; and Japanese Patent Application No. 2023-035605, filed on Mar. 8, 2023, the entire contents of all of which are incorporated herein by reference.

FIELD

Embodiments disclosed in the present specification and the drawings relate to a time phase determination apparatus and a time phase determination method.

BACKGROUND

Dynamic contrast-enhanced magnetic resonance imaging has been widely used conventionally in the examination and diagnosis of diseases. In the diagnosis using the dynamic contrast-enhanced magnetic resonance imaging, it is essential to acquire images of time phases related to the arrival time of a contrast agent, such as arterial phase (AP) images. Therefore, techniques to specify the range of the arterial phase are widely required.

In contrast to this, in the conventional workflow for the existing clinical scanning, scanning starts at constant time intervals after injection of a contrast agent, which does not take into account individual differences in peak arrival time of the arterial enhancement, making it difficult to specify the optimal arterial phase.

On the other hand, a fast reconstruction technique with high temporal resolution has been proposed to specify the optimal arterial phase for each subject. In this technique, the range of the arterial phase is detected in a series of fast reconstructed low-quality images, and high-quality images are finely reconstructed within this range, resulting in highly efficient and accurate scanning and reconstruction workflow.

However, the fast image reconstruction with the high temporal resolution requires a large amount of data, and manual selection of the arterial phase is difficult. In addition, the images obtained by the fast image reconstruction are less clear about the structures of organs, vessels, etc., and contain more noises and artifacts compared to the image quality of the diagnosis images. Thus, it is difficult to accurately detect the hepatic artery and portal vein.

Therefore, an automatic arterial phase range detection algorithm suitable for the fast image reconstruction is very important.

BRIEF DESCRIPTION OF THE DRAWINGS

FIG. 10 is a curve diagram of one specific example of a TIC corresponding to the liver area;

FIGS. 11A, 11B, 11C, and 11D are diagrams illustrating an example of expressing the order of enhancing organs corresponding to regions of interest.

DETAILED DESCRIPTION

Figure 1:
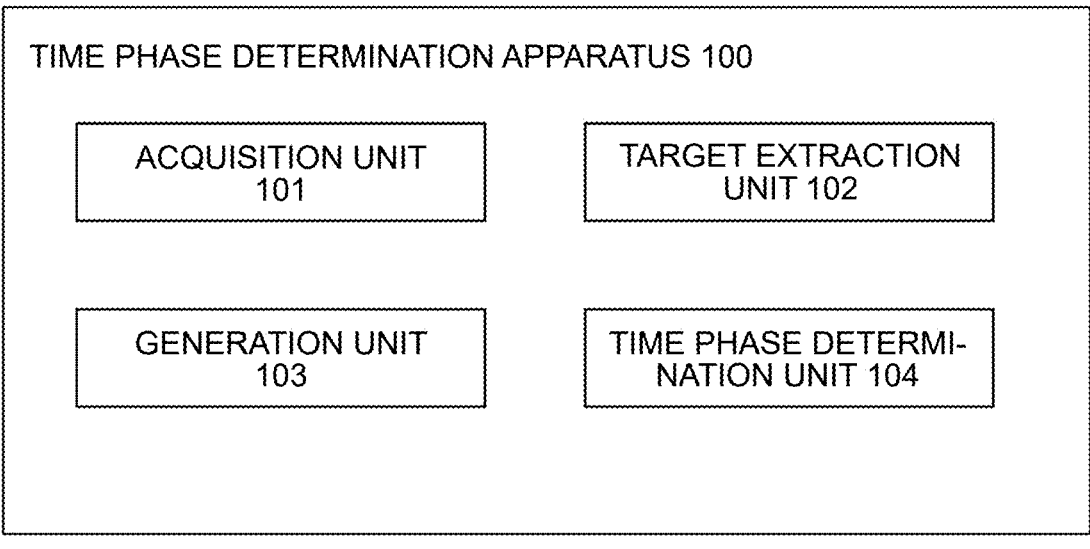
FIG. 1 is a block diagram illustrating a functional structure of a time phase determination apparatus according to a first embodiment.

A time phase determination apparatus according to an embodiment is a time phase determination apparatus for determining the range of a particular time phase in a contrast-enhanced image, and includes an acquisition unit, a target extraction unit, a generation unit, and a time phase determination unit. The acquisition unit acquires medical images at a plurality of different timings. The target extraction unit extracts a plurality of regions of interest on the basis of the medical images at the different timings. The generation unit generates a plurality of time intensity curves that are time intensity curves corresponding to the respective regions of interest. The time phase determination unit determines the range of the particular time phase on the basis of the time intensity curves.

Embodiments of the time phase determination apparatus and a time phase determination method are hereinafter described in detail with reference to the drawings.

Usually, the existing technology only analyzes a single organ tissue or vessel to detect the peak time phase of the time intensity curve (TIC) or the inflow and outflow time phases of the contrast agent. For example, only the TIC of the artery is analyzed and the enhanced state of a portal vein or a liver is not analyzed. However, depending on the individual difference of each subject, the liver may begin to be enhanced or may still be unenhanced when the TIC of the artery reaches its peak value. On the other hand, since a malignant liver tissue or the like has its blood mainly donated from the artery, focusing only on the TIC of the artery may miss the optimal tissue-to-tissue contrast.

In addition, the existing technique analyzes only a local region of interest (ROI) of the organ tissue or the vessel, and does not take into account the possibility of inhomogeneous distribution of the contrast agent within the vessel or organ. In addition, it is difficult to stably detect the accurate local ROI with the fast image reconstruction with high temporal resolution because of the low image quality.

Moreover, the existing technical literatures generally assume that the subject is holding his/her breath, and do not take into account measurement errors due to displacement of an organ tissue between scan images at the respective time points in the case of a respiratory motion.

For example, in Patent Literature 1, the time phases of inflow and outflow of the contrast agent are detected through analysis by approximating the TIC to a sigmoid function; however, the actual TIC has a large gap from the sigmoid function. In addition, in Patent Literature 1, only a single vessel is analyzed and the enhanced state of the other tissues is ignored. Moreover, in Patent Literature 1, the image quality is low, and situations in which images are reconstructed at high speed and free-breathing situations are not taken into account.

In Non-Patent Literature 1, the pixels of the artery are extracted on the basis of the maximum intensity projection (MIP) image of an image in an AX plane and the TIC of the pixels. However, in Non-Patent Literature 1, only the curve that reaches the peak value the earliest among the TICs for the single vessel is used, and the enhanced state of the other tissues is ignored. In addition, in Non-Patent Literature 1, the image quality is low, and situations in which images are reconstructed at high speed and free-breathing situations are not taken into account.

Moreover, in Non-Patent Literature 2, the optimal time phase is specified by classifying a single time phase. However, in Non-Patent Literature 2, the detection accuracy of the optimal time phase depends on the temporal resolution of the image sequence, and since only the local ROI is targeted, the detection accuracy may be affected by inhomogeneity of the contrast agent. In addition, in Non-Patent Literature 2, the image quality is low, and situations in which images are reconstructed at high speed and free-breathing situations are not taken into account.

In this regard, the technique disclosed in this application provides a time phase determination apparatus and a time phase determination method.

A time phase determination apparatus according to one aspect is a time phase determination apparatus configured to determine a range of a particular time phase in a contrast-enhanced image, the time phase determination apparatus including: an acquisition unit that acquires medical images at a plurality of different timings; a target extraction unit that extracts a plurality of regions of interest, based on the medical images at the different timings; a generation unit that generates a plurality of time intensity curves that are time intensity curves corresponding to the respective regions of interest; and a time phase determination unit that determines the range of the particular time phase, based on the time intensity curves.

Thus, the regions of interest can be comprehensively analyzed according to individual differences and the range of the time phase with the optimal contrast can be specified.

In the time phase determination apparatus according to one aspect, the target extraction unit may extract a first region of interest and a second region of interest that is enhanced by a contrast agent earlier than the first region of interest, and the time phase determination unit may determine a start time phase in the range of the particular time phase, based on the time intensity curve corresponding to the second region of interest and determine an end time phase in the range of the particular time phase, based on the time intensity curve corresponding to the first region of interest.

Thus, the regions of interest that are enhanced by the contrast agent at different times can be comprehensively analyzed and the range of the time phase with the optimal contrast can be specified.

In the time phase determination apparatus according to one aspect, the target extraction unit may extract a liver region as the first region of interest and an abdominal aorta region as the second region of interest.

This makes it possible to detect the optimal vessel segment and organ region and to specify the range of the suitable time phase for sure.

In the time phase determination apparatus according to one aspect, the target extraction unit may extract a first region of interest and a second region of interest that is enhanced by a contrast agent earlier than the first region of interest, the generation unit may generate the time intensity curve for an intensity difference between the first region of interest and the second region of interest, and the time phase determination unit may determine the range of the particular time phase, based on the time intensity curve for the intensity difference.

Thus, the regions of interest that are enhanced by the contrast agent at different times can be comprehensively analyzed and the suitable range of the time phase can be extracted based on the accurate TIC.

In the time phase determination apparatus according to one aspect, the target extraction unit may extract the liver region as the first region of interest and the related organ region related to the liver as the second region of interest.

Thus, when it is difficult to detect the optimum vessel segment, a plurality of organ areas can be targeted for detection, and the range of the suitable time phase can be determined for sure.

In the time phase determination apparatus according to one aspect, the target extraction unit may extract at least one region of interest among the regions of interest by (i) tracking a rigid body motion of an entire area of the region of interest, based on the medical images at the different timings, and (ii) calculating displacement of the region of interest relative to the entire area for each of the medical images at the different timings.

Thus, the entire region of interest can be tracked with a coarse-to-fine approach, reducing errors due to respiratory motion and the inhomogeneity of the contrast agent.

In addition, in the time phase determination apparatus according to one aspect, in the (i), the target extraction unit may track the rigid body motion of the entire area by extracting the entire area from one medical image, creating a binary template of a local target in the entire area, and obtaining a displacement quantity of the local target by performing template matching with the binary template in another medical image, and in the (ii), the target extraction unit may calculate the displacement of the region of interest relative to the entire area by extracting a plurality of local targets in the entire area and predicting the displacement of each of the local targets using a regression model.

Thus, the feasibility of tracking the entire region of interest with a coarse-to-fine approach can be improved.

In the time phase determination apparatus according to one aspect, the target extraction unit may select the regions of interest, based on the image resolution of the medical images at the different timings.

Thus, the suitable regions of interest can be selected according to differences in image quality of an image.

The time phase determination apparatus according to one aspect may further include an image reconstruction unit that reconstructs the medical image that has image resolution higher than a predetermined threshold and that is within the range of the particular time phase.

Thus, high-quality images can be reconstructed for the range of the suitable time phase to facilitate a commensurate disease diagnosis.

A time phase determination method according to one aspect is a time phase determination method for determining a range of a particular time phase in a contrast-enhanced image, the time phase determination method including: an acquiring step of acquiring medical images at a plurality of different timings; a target extracting step of extracting a plurality of regions of interest, based on the medical images at the different timings; a generating step of generating a plurality of time intensity curves that are time intensity curves corresponding to the respective regions of interest; and a time phase determining step of determining the range of the particular time phase, based on the time intensity curves.

Thus, the regions of interest can be comprehensively analyzed according to individual differences and the range of the time phase with the optimal contrast can be specified.

The technique disclosed in this application will be described below more specifically by combining the drawings, the embodiments, and specific examples. The following embodiments and specific examples are examples given to help understanding of the technique disclosed in this application, and are not intended to limit the technique disclosed in this application. In the specific embodiments, the components in the apparatus can be changed, merged, deleted or added according to the actual situation, and the steps of the method can also be changed, merged, deleted, added, or reordered according to the actual situation. The size and direction, etc. in the drawings are illustrative and can be changed according to the actual situation.

The time phase determination apparatus according to the technique disclosed in the present application is formed by a plurality of functional units, and is implemented in a device including a central processing unit (CPU) and a memory, such as an independent computer, as software or implemented dispersedly in a plurality of devices and implemented when each functional unit of the time phase determination apparatus stored in a memory is executed by any processor. Alternatively, the time phase determination apparatus according to the technique disclosed in this application is implemented in the form of hardware as circuitry capable of executing each function of the time phase determination apparatus. Here, the circuitry that implements the time phase determination apparatus can receive and send, or collect data via a network such as the Internet. Alternatively, the time phase determination apparatus according to the technique disclosed in this application may implement the function of each unit of the time phase determination apparatus by causing a processor of a computer to execute a computer program stored in advance in a storage medium.

First Embodiment

FIG. 1 is a block diagram illustrating a functional structure of a time phase determination apparatus 100 according to a first embodiment. As illustrated in FIG. 1, the time phase determination apparatus 100 includes an acquisition unit 101, a target extraction unit 102, a generation unit 103, and a time phase determination unit 104. The time phase determination apparatus 100 is used to determine the range of a particular time phase in a contrast-enhanced image. The so-called time phase here is a technical term that expresses the circumstance in which the contrast agent reaches, and the range of the time phase corresponds to the contrast-enhanced image taken in at least one timing.

The acquisition unit 101 acquires medical images at a plurality of different timings. For example, the acquisition unit 101 collects medical images from a medical image collection apparatus such as a computed tomography (CT) apparatus or a magnetic resonance imaging (MRI) apparatus via a wired or wireless communication link. The acquisition unit 101 may be a medical image collection apparatus itself with the function to communicate with the outside. The acquisition unit 101 may also determine a region of the medical image from the scan range collected by the medical image collection apparatus.

Here, the medical images at the different timings acquired by the acquisition unit 101 correspond to, for example, a plurality of medical images before and after the contrast agent reaches a predetermined area of a subject (for example, patient) that is the subject of a disease test or diagnosis. That is to say, the medical images include contrast-enhanced images. In a broad sense, the acquisition unit 101 only needs to acquire an enhanced image (contrast-enhanced image) of a tissue or an organ obtained using a contrast agent, and the principle of collection of the enhanced image and the type of contrast agent are not limited.

The medical image acquired by the acquisition unit 101, which is, for example, a three-dimensional image, may alternatively be a two-dimensional image depending on the principle of image collection. When the medical images are acquired from the MRI apparatus, the medical images are, for example, three-dimensional images that can be decomposed into a coronal plane (CO) image, a sagittal plane (SG) image, and an axial plane (AX) image.

The timing at which the acquisition unit 101 acquires the medical images is, for example, a timing for each predetermined time interval. The medical images acquired at high frequencies, i.e., with high temporal resolution, are preferred in terms of accuracy in acquiring the range of a particular time phase, as described below. In addition, medical images with low image resolution should be acquired if reduction of processing volume and data volume is considered. For example, the acquisition unit 101 acquires fast reconstructed images with high temporal resolution and low image resolution.

The target extraction unit 102 extracts a plurality of regions of interest on the basis of the medical images at the different timings acquired by the acquisition unit 101. Here, the so-called region of interest is, for example, a vessel segment region, a tissue region, or an organ region in the medical images. The region of interest may be the entire vessel segment region or the entire organ region, or may be a local region (local ROI) in the vessel segment, the tissue, and the organ. Here, the regions of interest correspond to different areas in the medical image, and the respective regions of interest are enhanced by the contrast agent at different timings due to the influence of blood flow or the like. For example, the regions of interest in the medical images at the different timings are different from each other in intensity.

Specifically, the target extraction unit 102 extracts each of the regions of interest using an image processing technique. Here, the method of the image processing is not limited, and methods such as dividing by machine learning or deep learning, or conventional image processing may be used, for example. The target extraction unit 102 may extract a certain region of interest on the basis of an image characteristic such as an intensity characteristic that is expressed when that region of interest is enhanced by the contrast agent, or may extract a certain region of interest on the basis of the image characteristic of that region of interest, such as a shape characteristic, independently of the enhancement by the contrast agent. Here, the certain region of interest may be acquired within each frame of the medical images, or may be acquired dynamically by analyzing changes between frames. The location where the certain region of interest exists may be different for each frame of the medical images.

For example, the target extraction unit 102 selects the regions of interest on the basis of the image resolution of the medical images at the different timings. For example, when the image resolution is lower than a certain level, it is difficult to accurately divide the vessel segment of the portal vein, hepatic artery, or the like; therefore, the target extraction unit 102 extracts the wider range, for example the organ area with the image characteristic of liver, kidney, or pancreas as the region of interest. In another example, when the image resolution has a certain level, the specific vessel segment cannot be divided accurately but the target extraction unit 102 extracts the vessel segment area that is superior to the specific vessel segment, such as aorta, as the region of interest. That is to say, the target extraction unit 102 extracts the vessel segments, tissues, or organs in smaller ranges as the regions of interest along with the increase of the image resolution. Thus, the suitable regions of interest can be selected in accordance with differences in image quality of the image.

For example, the target extraction unit 102 extracts multiple regions of interest in which the contrast is enhanced by the contrast agent at different timings. Here, that the timing of the enhancement by the contrast agent is different means, for example, the timing at which the intensity of the region of interest exceeds a certain predetermined threshold is different due to the contrast agent. For example, the target extraction unit 102 extracts the first region of interest and the second region of interest that is enhanced by the contrast agent earlier than the first region of interest. The number of regions of interest is two or more but is not limited to the particular number.

For example, the target extraction unit 102 may select the regions of interest on the basis of the range of a particular time phase that needs to be determined by the subsequent time phase determination unit 104.

The generation unit 103 generates a plurality of TICs that are TICs corresponding to the respective regions of interest. For example, for each region of interest, the generation unit 103 first calculates the representative value of the respective pixels in the region of interest for each medical image. Here, one example of the representative value is the average value of the intensity of the respective pixels in the region of interest. The generation unit 103 will then use the change in the representative value with the scanning timing of the medical image as the initial TIC of the region of interest. The generation unit 103 then performs predetermined preprocessing such as normalization, interpolation, or smoothing on the obtained initial TIC, and the curve for which the preprocessing has been performed is used as the TIC.

The method by which the generation unit 103 generates the TIC is not limited. For example, the generation unit 103 may not perform the aforementioned preprocessing, and the initial TIC, which is a line graph corresponding to the representative values of the pixels in the region of interest, may be used as the TIC.

The time phase determination unit 104 determines the range of the particular time phase on the basis of the TICs generated by the generation unit 103. Here, the so-called range of the particular time phase is the range of the time phase corresponding to the use scene of the contrast-enhanced image, such as an arterial phase (AP) or a portal venous phase (PVP), depending on the need for diagnosis of different diseases and other applications.

In the example of examination and diagnosis for the liver disease, the so-called arterial phase is the period in which the hepatic artery and its branches are fully enhanced but the hepatic veins are not enhanced in the antegrade flow. Here, the arterial phase includes an early arterial phase (early AP) and a late arterial phase (late AP). Of these phases, the portal vein is not yet enhanced in the early arterial phase. In the late arterial phase, on the other hand, the portal vein is enhanced. In clinical applications, when selecting the optimal arterial phase, it is necessary to obtain at least the period of the early arterial phase as the range of the particular time phase, since a good contrast between different tissues is desirable to analyze the hemodynamics of the lesion tissue. The so-called portal venous phase is the period in which the portal vein is fully enhanced but the hepatic vein is not enhanced in the antegrade flow, and is after a predetermined time of the arterial phase range. Thus, the range of detecting the arterial phase is also the basis of the range of detecting the portal venous phase.

Here, the range of the optimal arterial or portal phase or the like is not equal to a certain time after a certain vessel segment is enhanced because of individual differences.

For example, the time phase determination unit 104 determines the start time phase in the range of a particular time phase using the TIC corresponding to at least one region of interest among the TICs on the basis of the enhanced characteristic in the range of the particular time phase, and determines the end time phase in the range of the particular time phase using the TIC corresponding to at least one region of interest that is different from the at least one region of interest among the TICs. For example, when the regions of interest include the first region of interest and the second region of interest enhanced by the contrast agent earlier than the first region of interest, the time phase determination unit 104 determines the start time phase in the range of the particular time phase on the basis of the TIC corresponding to the second region of interest, and determines the end time phase in the range of the particular time phase on the basis of the TIC corresponding to the first region of interest. Thus, the regions of interest that are enhanced by the contrast agent at different times can be comprehensively analyzed and the range of the time phase with the optimal contrast can be specified.

The time phase determination unit 104 may determine the range of the time phase corresponding to the timing of scanning a single contrast-enhanced image, without being limited to the range of time phases corresponding to the timing of scanning multiple contrast-enhanced images. In this case, the start time phase is the end time phase. The time phase determination unit 104 may also determine the range of multiple intermittent time phases, for example, the range of time phases corresponding to early and late arterial phases without being limited to the range of the time phases corresponding to continuous time frames.

Here, the range of the particular time phase determined by the time phase determination unit 104 corresponds to at least one medical image (contrast-enhanced image), making it easier to detect a particular medical image, which can be used to examine or diagnose a specific disease.

Thus, the time phase determination apparatus 100 according to the first embodiment determines the range of the particular time phase using each of the TICs corresponding to the respective regions of interest; therefore, the regions of interest can be comprehensively analyzed in accordance with the individual differences and the range of the time phase with the optimum contrast can be specified.

Figure 2:
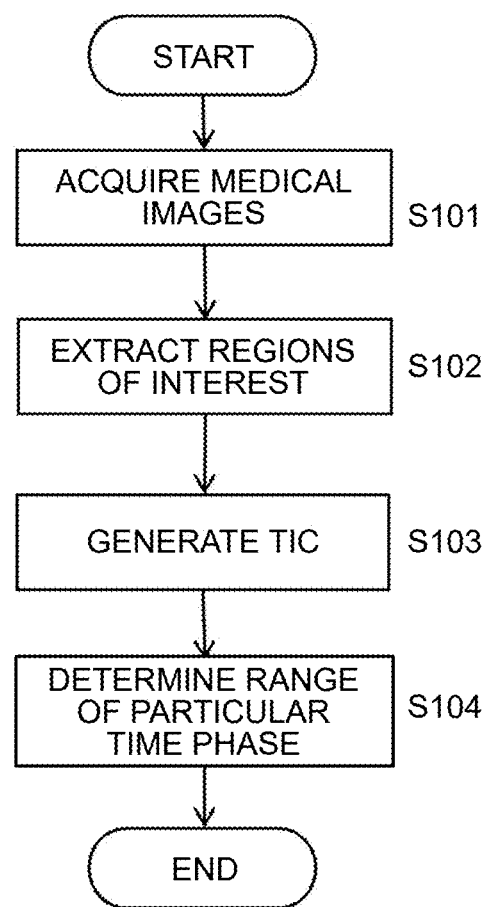
FIG. 2 is a flowchart expressing a time phase determination method implemented by the time phase determination apparatus according to the first embodiment.

With reference to FIG. 2, a time phase determination method to be implemented by the time phase determination apparatus 100 according to the first embodiment is described below. FIG. 2 is a flowchart expressing the time phase determination method implemented by the time phase determination apparatus 100 according to the first embodiment.

The time phase determination method in FIG. 2 is used to determine the range of the particular time phase in the contrast-enhanced image. First, at step S101, the acquisition unit 101 acquires the medical images at the different timings. Next, at step S102, the target extraction unit 102 extracts the regions of interest on the basis of the medical images acquired at the different timings. Next, at step S103, the generation unit 103 generates TICs corresponding to the respective regions of interest. Next, at step S104, the time phase determination unit 104 determines the range of a particular time phase on the basis of the generated TICs.

Thus, by the time phase determination method, the same effect as that of the time phase determination apparatus 100 described above can be obtained.

Second Embodiment

Figures 3, 4:
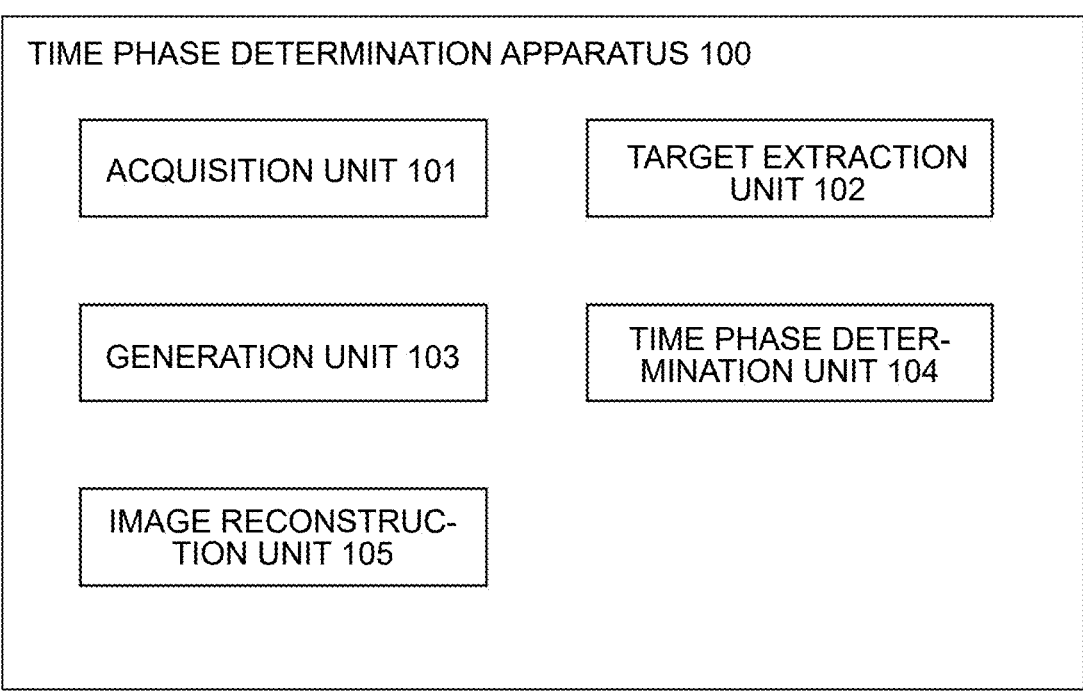
FIG. 3 is a block diagram illustrating a functional structure of a time phase determination apparatus according to a second embodiment.
FIG. 4 is a flowchart illustrating a process in which a target extraction unit extracts a liver area.

A second embodiment of the present application is described below with reference to FIG. 3. FIG. 3 is a block diagram illustrating a functional structure of a time phase determination apparatus 110 according to a second embodiment. Here, the functional unit in the time phase determination apparatus 110 that is the same as the functional structure described in the first embodiment is denoted with the same reference symbol in the drawing and the detailed description is omitted. As illustrated in FIG. 3, this embodiment differs from the first embodiment in that the time phase determination apparatus 110 further includes an image reconstruction unit 105.

The image reconstruction unit 105 reconstructs medical images whose image resolution is higher than a predetermined threshold and which is within the range of a particular time phase determined by the time phase determination unit 104.

That is to say, when the time phase determination unit 104 of the time phase determination apparatus 100 according to the first embodiment determines the range of the particular time phase, the medical image within the range of the particular time phase can be used for the relevant application; however, the medical image acquired by the acquisition unit 101 is used as it is. The medical image acquired by the acquisition unit 101 is the image for determining the range of the particular time phase and may be characterized by high temporal resolution but low image resolution, depending on the actual computing power and computational speed of the device. For example, the medical images acquired by the acquisition unit 101 are continuously changing images obtained based on the fast reconstruction. Therefore, if the medical images acquired by the acquisition unit 101 are used as they are, they may have large noise and artifacts and may not meet the needs of applications such as diagnosis of diseases.

In contrast, in the second embodiment, after the time phase determination unit 104 determines the range of the particular time phase, the image reconstruction unit 105 reconstructs the medical image whose image resolution is higher than a predetermined threshold so that the image meets the needs of various applications such as diagnosis of diseases within the range of the particular time phase.

Here, the image reconstructed by the image reconstruction unit 105 may be each of the medical images acquired by the acquisition unit 101 that are within the range of the particular time phase, or a portion thereof. At least one medical image with the high image resolution within the range of the particular time phase may be reconstructed by a method different from the medical images acquired by the acquisition unit 101.

Thus, the same effect as that in the first embodiment can be obtained, and the image with the high quality for the range of the suitable time phase can be reconstructed so as to facilitate the diagnosis of the corresponding disease.

Specific examples of the embodiment are hereinafter described using the arterial phase of the liver detected from three-dimensional medical images acquired by the MRI apparatus as the particular time phase.

In detecting the arterial phase of the liver, it is desirable to obtain a time frame in which the hepatic artery is fully enhanced but the portal vein is not enhanced, as described above. Additionally, due to individual differences, the portal vein may begin to be enhanced or may still be unenhanced when the hepatic artery reaches its peak. Depending on the different image resolutions due to the fast reconstruction, etc., the hepatic artery and portal vein may not be accurately extracted, and in this case, other organs or vessel segments are extracted instead of the hepatic artery and portal vein.

First Specific Example

In a first specific example, the target extraction unit 102 extracts a liver area as the first region of interest and an abdominal aorta area as the second region of interest that is enhanced by the contrast agent earlier than the first region of interest.

After the medical images are acquired by the acquisition unit 101, the target extraction unit 102 extracts the liver area as the first region of interest, and this process is described first.

FIG. 4 is a flowchart illustrating the process in which the target extraction unit 102 extracts the liver area. As illustrated in FIG. 4, at step S210, the target extraction unit 102 tracks the rigid body motion of the entire area of the liver area, based on the medical images acquired by the acquisition unit 101 at the different timings according to the temporal changes of the liver position due to the influence of free breathing or the like.

Figure 5:
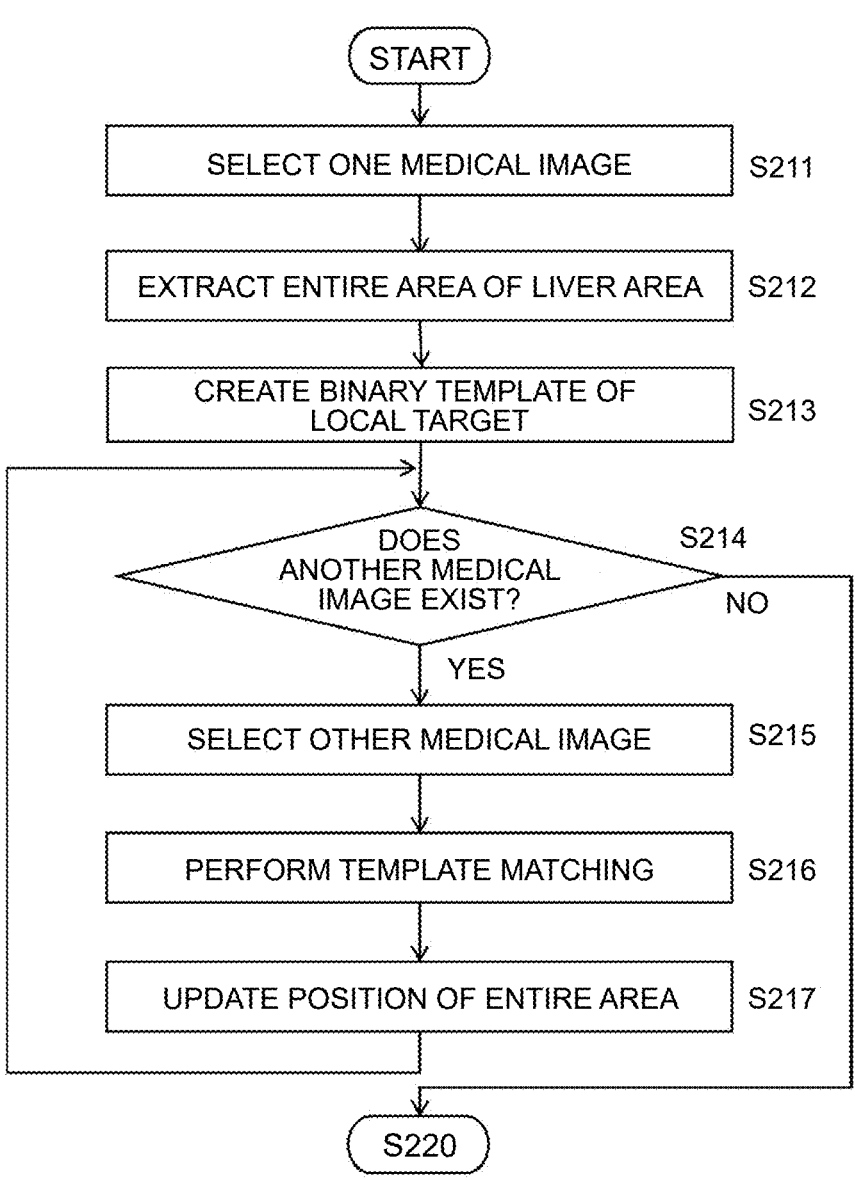
FIG. 5 is a flowchart illustrating a specific example of tracking a rigid body motion of an entire area of the liver area.

Specifically, the target extraction unit 102, for example, tracks the rigid body motion of the entire area of the liver area according to the procedure in FIG. 5. FIG. 5 is a flowchart illustrating a specific example of tracking the rigid body motion of the entire area of the liver area.

As illustrated in FIG. 5, at step S211, the target extraction unit 102 selects one of the medical images. In one example, the target extraction unit 102 may select one of the medical images on the basis of the intensity characteristic of the liver area in the image. In another example, the target extraction unit 102 may select the first medical image corresponding to the state before the contrast enhancement. In still another example, the target extraction unit 102 may select one medical image according to a predetermined rule on the basis of the intensity characteristic of the liver area in the image.

At step S212, the target extraction unit 102 extracts the entire area of the liver area from the one medical image selected at step S211. For example, the target extraction unit 102 may extract the entire area of the liver area using a conventional image processing method on the basis of the intensity characteristic of the liver area in the image. The target extraction unit 102 may also extract the entire area of the liver area on the basis of a division algorithm obtained by machine learning or deep learning. For example, the target extraction unit 102 may extract the entire area of the liver area in a three-dimensional space by extracting the entire area of the liver area from each of the CO image, the SG image, and the AX image.

At step S213, the target extraction unit 102 creates a binary template of the local target in the entire area of the liver area. Here, the local target in the entire area of the liver area is, for example, a patch at the edge of the liver area, and a part of the patch is located in the entire area of the liver area.

Figure 6A:
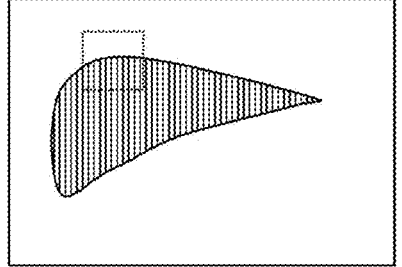
FIGS. 6A, 6B, 6C, and 6D are diagrams illustrating an example of binary template matching.

FIGS. 6A, 6B, 6C, and 6D are diagrams illustrating an example of binary template matching. For example, as illustrated in FIG. 6A, the target extraction unit 102 considers the area within a dashed-line frame in the CO image to be the local target. The local target is a vertex patch located at the edge of the liver area.

Figure 6B:

Then, for example, as illustrated in FIG. 6B, the target extraction unit 102 creates a binary template of the vertex patch by binarizing the intensity diagram of the vertex patch to section the portion of the liver area. In other medical images, the intensity of the vertex patch changes due to the influence of the contrast agent; however, the use of the binary template improves the robustness of the algorithm against the change of the contrast agent.

Although the example of the CO image is illustrated in FIGS. 6A, 6B, 6C, and 6D, the target extraction unit 102 creates the binary template regarding the CO image, the SG image, etc.

At step S214, the target extraction unit 102 determines whether another medical image exists. If another medical image exists (Yes at step S214), the target extraction unit 102 selects the other medical image at step S215. For example, if the target extraction unit 102 selects the first medical image corresponding to the state before the contrast enhancement at step S211, the target extraction unit 102 selects the next medical image in time order at step S215.

Figure 6C:
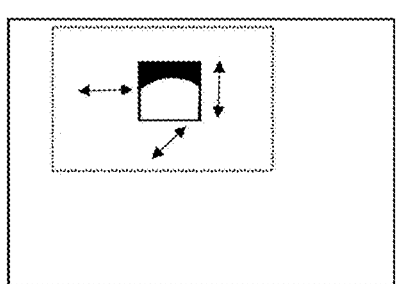

At step S216, the target extraction unit 102 performs template matching using the binary template of the local target in the other medical image selected at step S215 to obtain the displacement quantity of the local target. For example, the target extraction unit 102 tracks the motion of the vertex patch by searching for the position matching the vertex patch in the other medical image to acquire the displacement (x, y, z) of the vertex patch. Here, the displacement in an X direction is determined by the CO image. The displacement in a Y direction is determined by the SG image. The displacement in a Z direction is determined by combining the CO image and the SG image. FIG. 6C illustrates an example of the template matching on three orthogonal directions, and expresses the range of the template matching search with a dashed-line frame.

The algorithm for the template matching is not limited and may be implemented, for example, by a squared difference matching method or a relational coefficient matching method.

Figure 6D:
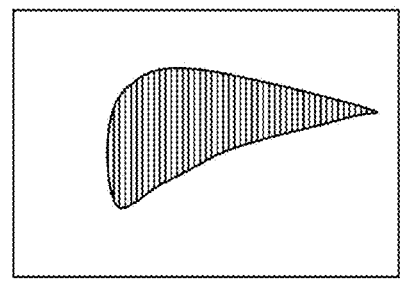

At step S217, the target extraction unit 102 updates the location of the entire area of the liver area. Specifically, the target extraction unit 102 uses the displacement quantity of the local target obtained at step S216 as the overall displacement quantity and moves the entire area extracted at step S212 by the corresponding quantity. FIG. 6D illustrates an example of the state of the entire area of the liver area after the rigid body displacement.

Then, back to step S214, the target extraction unit 102 updates the position of the entire area for all the medical images (No at step S214) and then the process advances to step S220.

The procedure in FIG. 5 is one example of the tracking process at step S210, and the tracking process may be performed in any other way. However, considering the data volume of the three-dimensional images and the influence of the contrast agent, it is desirable that the robustness be improved while the processing volume is reduced efficiently in the template matching of the binary template.

Back to FIG. 4, at step S220, the target extraction unit 102 calculates the displacement of the liver area relative to the entire area of the liver area for each of the medical images at the different timings. That is to say, the target extraction unit 102 updates the actual liver area in each of the medical images.

Figure 7:
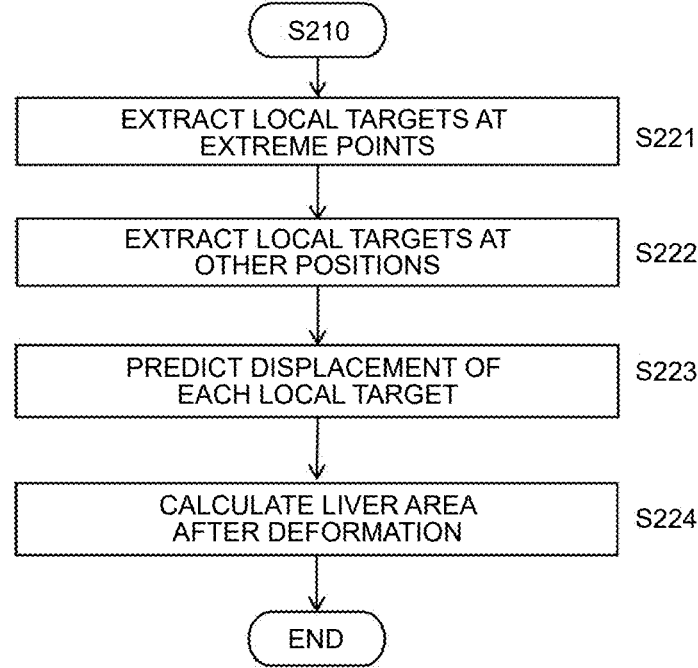
FIG. 7 is a flowchart illustrating one specific example of calculating displacement of the liver area relative to the entire area.

Specifically, the target extraction unit 102 updates the actual liver area in each medical image, for example, according to the procedure in FIG. 7. FIG. 7 is a flowchart illustrating one specific example of calculating the displacement of the liver area relative to the entire area.

As illustrated in FIG. 7, at step S221, the target extraction unit 102 extracts a plurality of local targets at extreme points in the entire area of the liver area regarding the entire area of the liver area within the medical image extracted at step S210. Here, the local target is, for example, a 3D patch or super voxel. The extreme point is the location corresponding to the position that is regarded as the vertex of the liver area, and the location of the vertex indicates the vertex of the shape in a broad sense, not the uppermost point of the liver.

Figure 8A:
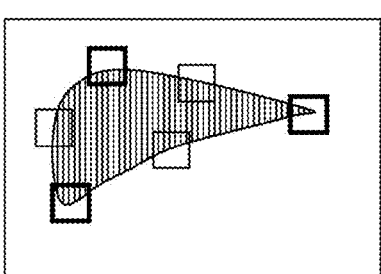
FIGS. 8A, 8B, and 8C are diagrams illustrating an example of calculating an actual area of a liver using a regression model.
Figure 8B:
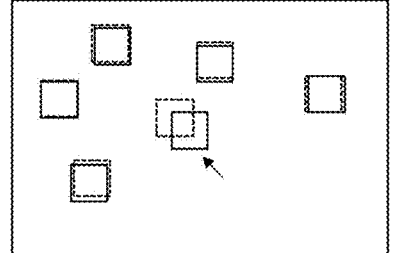
Figure 8C:
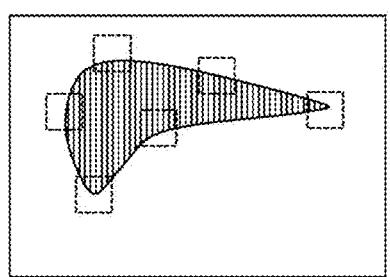

FIGS. 8A, 8B, and 8C are diagrams illustrating an example of calculating the actual area of the liver using a regression model. Here, FIGS. 8A, 8B, and 8C illustrate one example of the CO image. The local targets at the three extreme points are illustrated exemplarily with thick frames in FIG. 8A.

At step S222, on the basis of the local targets located at the extreme points, the target extraction unit 102 collects a plurality of local targets at other positions. For example, by sampling between two local targets located at the extreme points, some local targets located at the boundaries of the entire area of the liver area are extracted uniformly. FIG. 8A illustrates an example of the three local targets at the other positions with thin frames.

Thus, down-sampling of the liver area is achieved by collecting the local targets.

The processes at steps S221 and S222 may be performed together, and the local targets may be extracted by another method.

At step S223, the target extraction unit 102 predicts the displacement of each of the local targets extracted at steps S221 and S222 using a regression model. The method of implementing the algorithm of the regression model is not limited and, for example, a trained regression model based on machine learning or deep learning may be used.

In the regression model, the displacements of the adjacent local targets can be updated simultaneously in each prediction. In addition, by limiting the curvature change of the local target, the influence of noise is reduced and the efficiency can be improved. In a case where the entire area of the liver area is extracted from the first image before the contrast enhancement at steps S211 and S212 in FIG. 5, the wrong division may occur in dividing the liver area in the image before the contrast enhancement; however, by analyzing the local target near the organ that is enhanced by the contrast agent earlier than the liver, the wrong division can be corrected efficiently without limiting the curvature change. The accuracy of displacement measurement can be improved by adding an intensity enhancement characteristic for each pixel between the medical images.

FIG. 8B illustrates an example of how the regression model is used to predict each of the local targets. Here, the initial positions of the local targets collected at steps S221 and S222 are expressed in solid-line frames, and the positions of the local targets modified by the regression model are expressed in dashed-line frames. The local target highlighted by an arrow has a large displacement; however, since this local target is adjacent to the kidney that is enhanced by the contrast agent earlier than the liver, its curvature change is not limited.

At step S224, the target extraction unit 102 calculates the liver area after deformation on the basis of the displacement of each local target. For example, the target extraction unit 102 acquires the deformed liver area by interpolating the modified local target. FIG. 8C illustrates an example of the liver area after deformation.

The procedure in FIG. 7 is an example of the displacement calculation process at step S220; however, the actual liver area may be calculated using any other image processing method. However, considering the data volume of three-dimensional images and the influence of the contrast agent, it is desirable to efficiently reduce the processing volume by extracting and down-sampling the local objects.

The completion of the procedure in FIG. 4 above allows the entire region of interest (liver) to be tracked in a coarse-to-fine approach, reducing errors due to a respiratory motion and variations in contrast agent distribution.

The acquisition of the medical images by the acquisition unit 101 is followed by the extraction of the abdominal aorta area by the target extraction unit 102 as the second region of interest, and this process is described next. Although the abdominal aorta is enhanced by the contrast agent earlier than the liver, the order of extraction of the abdominal aorta area and the liver area is not limited.

Here, if the target extraction unit 102 extracts and tracks the abdominal aorta area by the same method as that in the procedure in FIG. 4, the effect of the respiratory motion will be taken into account in the way similar to the aforementioned one. However, considering that the duration of the arterial phase is short, the abdominal aorta does not have to be processed for tracking because the influence of the respiratory motion is small within this time range.

As one specific example, the target extraction unit 102 uses the optimal vessel segment adjacent to the hepatic artery in the abdominal aorta as the second region of interest, and analyzes the enhanced state of that vessel segment to substantially reflect the enhanced state of the hepatic artery. For example, the target extraction unit 102 compares the images before and after the contrast agent reaches the abdominal aorta among the medical images, so that the area corresponding to the abdominal aorta (area adjacent to the hepatic artery) is detected in at least one image after the contrast agent reaches, and that pixel area is used as the second region of interest. The target extraction unit 102 still considers the pixel region to be the second region of interest also in another medical image.

This reduces the amount of processing because the tracking process is no longer necessary. Thus, the abdominal aortic area can be analyzed when it is difficult to accurately divide the hepatic artery due to the influence of image resolution. When the scan area of the magnetic resonance image is limited and the medical image includes only the liver and its surroundings, stable detection results can be obtained by using the liver area and abdominal aorta area as the regions of interest.

The generation unit 103 generates two initial TICs by calculating the intensity average value of the pixels within the abdominal aorta area (second region of interest) and the liver area (first region of interest). Here, the initial TIC is a line graph expressing the relationship between the time intensity (intensity average value in the area) and the timing of scanning the medical image.

The generation unit 103 then performs preprocessing, including normalization and interpolation, on the initial TIC. Here, smoothing may or may not be performed.

First, the generation unit 103 performs the normalization process by the expression $(SI_n-SI_0)/SI_0$.

In this expression, $SI_n$ represents the intensity average value in the region of interest in the medical image at the n-th timing, and $SI_0$ represents the intensity average value in the region of interest in the medical image (initial medical image) at the 0-th timing (n is an integer of 0 to N, and N is the total number of images).

Next, the generation unit 103 inserts some floating-point number data between the adjacent pieces of data in the TIC. The generation unit 103 then estimates the trend of the TIC change over time by interpolation and fitting.

The time phase determination unit 104 determines the start time phase in the range of the arterial phase of the liver using the TIC corresponding to the abdominal aortic area. For example, the time phase determination unit 104 sets the time phase of the maximum gradient of the TIC corresponding to the abdominal aortic area as the start time phase in the range of the arterial phase. The time phase determination unit 104 may also use the time phase in which the TIC corresponding to the abdominal aorta area exceeds a predetermined threshold as the start time phase in the range of the arterial phase of the liver.

Figure 9:
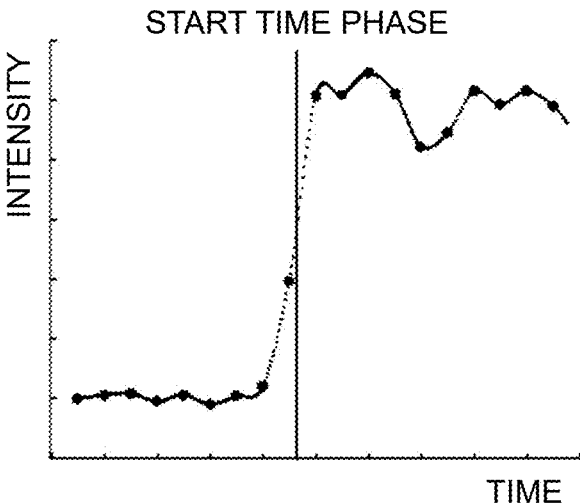
FIG. 9 is a curve diagram of one specific example of a TIC corresponding to an abdominal aorta area.

FIG. 9 is a curve diagram of one specific example of the TIC corresponding to the abdominal aorta area. FIG. 9 illustrates an example where the time phase of the maximum gradient is the start time phase in the range of the arterial phase.

The time phase determination unit 104 also determines the end time phase in the range of the arterial phase of the liver using the TIC corresponding to the liver area. For example, the time phase determination unit 104 sets the time phase in which the TIC value corresponding to the liver area increases to a predetermined threshold as the end time phase in the range of the arterial phase of the liver.

FIG. 10 is a curve diagram of one specific example of the TIC corresponding to the liver area. FIG. 10 illustrates an example where the time phase in which the numerical value increases to a predetermined threshold is the end time phase in the range of the arterial phase.

Thus, the entire area of the optimal vessel segment and organ can be targeted for detection and the range of the appropriate liver arterial phase can be determined.

Second specific example Next, another specific example of detecting the arterial phase of the liver from a three-dimensional medical image acquired by an MRI apparatus is described as a second specific example. Here, the detailed description of the same process as that in the first specific example is omitted.

For example, it may be difficult to extract the abdominal aorta area as described in the first specific example due to the influence of the contrast agent and the image resolution in the fast reconstruction. Thus, if the extraction of the abdominal aorta area is difficult, the related organs related to the liver may be extracted as the second region of interest.

Here, the relevant organ areas are, for example, organs that are enhanced by the contrast agent earlier than the liver (for example, kidney and pancreas).

The target extraction unit 102 extracts the related organ (for example, kidney) area related to the liver as the second region of interest.

FIGS. 11A, 11B, 11C, and 11D are diagrams illustrating an example of expressing the order of enhancing the organs corresponding to the regions of interest. FIGS. 11A, 11B, 11C, and 11D illustrate the order from the pre-contrast state to the fully enhanced liver. As illustrated in FIGS. 11A, 11B, 11C, and 11D, the kidneys are enhanced after the abdominal aorta but before the liver due to the operation of the contrast agent, so that the enhancement of the kidney area can also be used as a reference for the hepatic arterial phase.

Here, for example, the method by which the target extraction unit 102 extracts the kidney area is the same as the method used to extract the liver region. For example, the target extraction unit 102 tracks the displacement of the kidney area using a coarse-to-fine approach on the basis of methods such as dividing by machine learning or deep learning, or the conventional image processing methods.

The generation unit 103 generates the TIC for the intensity difference between the liver area and the kidney area.

The time phase determination unit 104 determines the range of the arterial phase of the liver on the basis of the TIC for the intensity difference between the liver area and the kidney area (hereafter, kidney area-liver area). Here, for example, the time phase determination unit 104 analyzes the TIC for the kidney area-liver area intensity difference to determine the range of the arterial phase of the liver.

Figure 12:
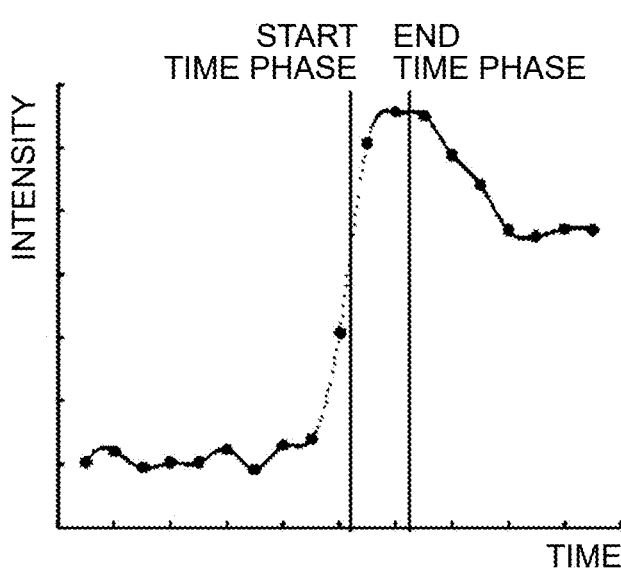
FIG. 12 is a curve diagram of one specific example of a TIC for an intensity difference between a kidney area and the liver area.

FIG. 12 is a curve diagram of one specific example of the TIC for the kidney area-liver area intensity difference. As illustrated in FIG. 12, the time phase determination unit 104 sets the time phase where the TIC for the intensity difference increases to a first threshold as the start time phase in the range of the arterial phase, and sets the time phase corresponding to the peak value of the TIC for the intensity difference (before the contrast between both decreases) as the end time phase in the range of the arterial phase. The time phase determination unit 104 may alternatively use the time phase in which the TIC for the intensity difference increases to a second threshold as the end time phase in the range of the arterial phase.

Thus, it is possible to deal with the situations where the detection of the optimal vessel segment is difficult, and the appropriate time phase range can be determined with multiple organ areas as detection targets.

Other Embodiments

The two specific examples described above may be combined. By combining the analysis result of the TIC for the intensity difference between the liver area and the kidney area (or pancreas, etc.) with the analysis result of the TIC of the abdominal aorta area, the highly accurate candidate time phase may be obtained. The start time phase and the end time phase obtained by multiple (differential) intensity curve analysis may be used as multiple candidate values. The reliability of each candidate value may be scored based on the statistical performance of each candidate value in the training data, and the optimal start/end time phase may be selected as the detection result, or a weighted average of the candidate values may be used as the detection result.

The above embodiments and specific examples have described the cases where the image resolution is insufficient, for example, for the fast reconstruction images. However, the medical images used in the technique disclosed in this application are not limited to the fast reconstructed images, and the portal vein and hepatic artery areas may be the regions of interest if the image has high quality or has sufficient imaging characteristics. If the portal vein and hepatic artery can be divided stably and accurately, the TICs can be analyzed based on the two division results to achieve more accurate arterial phase detection. For example, the start time phase is directly determined by the TIC of the hepatic artery, and the end time phase is determined by the TIC of the portal vein.

The above embodiments and specific examples have described the case in which the target extraction unit 102 extracts the regions of interest. However, the target extraction unit 102 may extract a plurality of local regions of interest (local ROIs) from one region of interest (for example, first region of interest), and the generation unit 103 may generate multiple TICs corresponding to the respective local regions of interest, so that the time phase determination unit 104 can determine a particular time phase as needed. For example, the target extraction unit 102 may extract the local regions of interest such as renal cortex and renal medulla from inside the kidney, and analyze the change of the intensity over time between the areas of the respective regions of interest and the change of the intensity contrast over time between the different areas, so as to specify the particular time phase of the arterial phase, a corticomedullary phase, or a nephrographic phase.

In the above embodiments and specific examples, the influence of free breathing has been described. However, the technique disclosed in this application can also be applied to a case where the subject holds his/her breath. In such a case, the organ tracking process is no longer necessary, thus reducing the amount of processing.

In the embodiments and specific examples described above, for example, the processing units of the acquisition unit 101, the target extraction unit 102, the generation unit 103, the time phase determination unit 104, and the image reconstruction unit 105 are implemented by the processing functions of processing circuitry provided in the time phase determination apparatus 100 or 110.

Here, the processing circuitry is implemented by, for example, a processor. In this case, the processing functions that implement the respective processing units described above are stored in storage circuitry in the form of computer programs that can be executed by a computer. The processing circuitry then reads out and executes each computer program stored in the storage circuitry to implement the processing function corresponding to each computer program. In other words, processing circuitry 143 having read out each computer program has each of the processing units illustrated in FIG. 1 or FIG. 3.

In addition, although the processing circuitry is implemented by a single processor in the description of the example, the embodiment is not limited to this example. In another example, the processing circuitry may be formed by a combination of a plurality of independent processors, and may implement each processing function by having each processor execute a computer program. The respective processing functions of the processing circuitry may be integrated or dispersed in a single unit or multiple units of processing circuitry as appropriate. Each processing function of the processing circuitry may be implemented by mixing of hardware such as circuitry and software. Although an example in which the computer program corresponding to each processing function is stored in a single unit of storage circuitry is described here, the embodiment is not limited to this example. In another example, computer programs corresponding to the respective processing functions may be dispersedly stored in multiple units of storage circuitry, and the processing circuitry may read out and execute the computer programs from the respective units of storage circuitry and execute the computer programs.

The term "processor" used in the above embodiment refers to, for example, circuitry such as a central processing unit (CPU), a graphics processing unit (GPU), an application specific integrated circuit (ASIC), a programmable logic device (for example, simple programmable logic device (SPLD)), a complex programmable logic device (CPLD), and a field programmable gate array (FPGA). Here, the computer program may be directly incorporated in the circuitry of the processor instead of being saved in the storage circuitry. In this case, the function is implemented when the processor reads out and executes the computer program incorporated in the circuitry. In addition, each processor in this embodiment is not limited to the processor configured as a single unit of circuitry for each processor, and may alternatively be configured as a single processor by combining multiple independent units of circuitry to implement the function.

Here, the computer program to be executed by the processor is provided by being incorporated in advance in a read only memory (ROM), storage circuitry, and the like. Note that this computer program may be provided by being recorded as files in a format that can be installed or executed in these devices in a computer-readable non-transitory storage medium such as a compact disc (CD)-ROM, a flexible disk (FD), a CD-R (recordable), or a digital versatile disc (DVD). This computer program may be provided or distributed by being stored on a computer connected to a network such as the Internet and downloaded through the network. For example, this computer program is formed by a module including each of the aforementioned processing functions. As the actual hardware, when the CPU reads out the computer program from the storage medium such as a ROM and executes the computer program, each module is loaded on the main storage device and generated on the main storage device.

In the embodiments and modifications described above, each component of each apparatus in the drawing is conceptual in terms of function and does not necessarily have to be physically configured as illustrated in the drawing. In other words, the specific form of integration or dispersion of each apparatus is not limited to that illustrated in the drawing, but can be configured by functionally or physically dispersing or integrating all or part of it in arbitrary units according to various loads and usage conditions. Furthermore, each processing function performed by each apparatus can be implemented, entirely or partially, by a CPU and a computer program analyzed and executed by the CPU, or by hardware using wired logic.

Among the processes described in the embodiments and modifications described above, the process that is described as being performed automatically can be, entirely or partially, performed manually or the process that is described as being performed manually can be, entirely or partially, performed automatically by a known method. Furthermore, the information including the process procedure, the control procedure, the specific names, and various kinds of data and parameters expressed in the above document and drawings can be changed arbitrarily unless specified otherwise.

Various kinds of data handled in this specification is typically digital data.

According to at least one embodiment described above, the range of the time phase with the optimum contrast can be specified.

While certain embodiments have been described, these embodiments have been presented by way of example only, and are not intended to limit the scope of the inventions. Indeed, the novel embodiments described herein may be embodied in a variety of other forms; furthermore, various omissions, substitutions, changes and combination thereof in the form of the embodiments described herein may be made without departing from the spirit of the inventions. The accompanying claims and their equivalents are intended to cover such forms or modifications as would fall within the scope and spirit of the inventions.

What is claimed is:

1. An image processing apparatus, comprising:
   processing circuitry configured to
   acquire a plurality of medical images, each of which corresponds to a different one of a plurality of timings;
   extract a first region of interest in each of the plurality of medical images;
   extract a second region of interest in each of the plurality of medical images, a timing when the second region of interest is enhanced by a contrast agent being earlier than a timing when the first region of interest is enhanced by the contrast agent;
   generate a first time intensity curve corresponding to a pixel value in the first region of interest at the plurality of timings;
   generate a second time intensity curve corresponding to a pixel value in the second region of interest at the plurality of timings; and
   determine a range of a time phase corresponding to a period before a first time phase and after a second time phase, the first time phase being a time phase when the first time intensity curve reaches a predetermined value from a value less than the predetermined value, the second time phase being determined based on a gradient of the second time intensity curve.

2. The image processing apparatus according to claim 1, wherein the processing circuitry is further configured to extract the first region of interest, which corresponds to a liver area and extract the second region of interest, which corresponds to an abdominal aorta area.

3. The image processing apparatus according to claim 1, wherein the processing circuitry is further configured to extract at least one region of interest among the first region of interest and the second region of interest by:
   tracking a rigid body motion of an entire area of the region of interest, based on the plurality of medical images; and
   calculating displacement of the region of interest relative to the entire area for each of the plurality of medical images.

4. The image processing apparatus according to claim 3, wherein the processing circuitry is further configured to:
   in the tracking, track the rigid body motion of the entire area by extracting the entire area from one medical image, creating a binary template of a local target in the entire area, and obtaining a displacement quantity of the local target by performing template matching with the binary template in another medical image, and
   in the calculating of the displacement, calculate the displacement of the region of interest relative to the entire area by extracting a plurality of local targets in the entire area and predicting the displacement of each of the local targets using a regression model.

5. The image processing apparatus according to claim 1, wherein the processing circuitry is further configured to select a region of interest to be extracted, based on an image resolution of the plurality of medical images.

6. The image processing apparatus according to claim 1, wherein the processing circuitry is further configured to reconstruct a medical image that has image resolution higher than an image resolution of the plurality of medical images, the medical image being within the determined range of the time phase.

7. The image processing apparatus according to claim 1, wherein the processing circuitry is further configured to reconstruct a medical image that has image resolution higher than an image resolution of the plurality of medical images, the medical image corresponding to a time phase determined based on the determined range of the time phase.

8. The image processing apparatus according to claim 1, wherein the second time phase is a time phase when the gradient of the second time intensity curve is maximum.

9. An image processing apparatus, comprising:
processing circuitry configured to
    acquire a plurality of medical images, each of which corresponds to a different one of a plurality of timings;
    extract a first region of interest in each of the plurality of medical images;
    extract a second region of interest in each of the plurality of medical images, a timing when the second region of interest is enhanced by a contrast agent being earlier than a timing when the first region of interest is enhanced by the contrast agent;
    generate a first time intensity curve corresponding to a pixel value in the first region of interest at the plurality of timings;
    generate a second time intensity curve corresponding to a pixel value in the second region of interest at the plurality of timings; and
    determine a range of a time phase corresponding to a period before a first time phase and after a second time phase, the first time phase being a time phase when the first time intensity curve reaches a first predetermined value from a value less than the first predetermined value, the second time phase being a time phase when the second time intensity curve reaches a second predetermined value from a value less than the second predetermined value.

10. The image processing apparatus according to claim 9, wherein the first region of interest corresponds to a liver area and the second region of interest corresponds to an abdominal aorta area.

11. The image processing apparatus according to claim 9, wherein the processing circuitry is further configured to extract at least one region of interest among the first region of interest and the second region of interest by:
    tracking a rigid body motion of an entire area of the region of interest, based on the plurality of medical images; and
    calculating displacement of the region of interest relative to the entire area for each of the plurality of medical images.

12. The image processing apparatus according to claim 11, wherein the processing circuitry is further configured to:
    in the tracking, track the rigid body motion of the entire area by extracting the entire area from one medical image, creating a binary template of a local target in the entire area, and obtaining a displacement quantity of the local target by performing template matching with the binary template in another medical image, and
    in the calculating of the displacement, calculate the displacement of the region of interest relative to the entire area by extracting a plurality of local targets in the entire area and predicting the displacement of each of the local targets using a regression model.

13. The image processing apparatus according to claim 9, wherein the processing circuitry is further configured to select a region of interest to be extracted, based on an image resolution of the plurality of medical images.

14. The image processing apparatus according to claim 9, wherein the processing circuitry is further configured to reconstruct a medical image that has an image resolution higher than an image resolution of the plurality of medical images, the medical image being within the determined range of the time phase.

15. The image processing apparatus according to claim 9, wherein the processing circuitry is further configured to reconstruct a medical image that has an image resolution higher than an image resolution of the plurality of medical images, the medical image corresponding to a time phase determined based on the determined range of the time phase.

* * * * *